(12) United States Patent
Oda et al.

(10) Patent No.: US 12,172,835 B2
(45) Date of Patent: Dec. 24, 2024

(54) MANAGEMENT SYSTEM, MANAGEMENT METHOD, AND PROGRAM

(71) Applicant: TOYOTA JIDOSHA KABUSHIKI KAISHA, Toyota Aichi-ken (JP)

(72) Inventors: Shiro Oda, Anjo Aichi-ken (JP); Tetsuya Taira, Nagakute Aichi-ken (JP); Satoshi Toyoshima, Okazaki Aichi-ken (JP); Yuta Watanabe, Toyota Aichi-ken (JP); Takeshi Matsui, Nisshin Aichi-ken (JP); Takayoshi Nasu, Okazaki Aichi-ken (JP); Kei Yoshikawa, Nagoya Aichi-ken (JP); Yusuke Ota, Nagakute Aichi-ken (JP); Yutaro Ishida, Toyota Aichi-ken (JP); Yuji Onuma, Nagoya Aichi-ken (JP); Kyosuke Arai, Toyota Aichi-ken (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 633 days.

(21) Appl. No.: 17/507,036

(22) Filed: Oct. 21, 2021

(65) Prior Publication Data
US 2022/0204268 A1 Jun. 30, 2022

(30) Foreign Application Priority Data
Dec. 24, 2020 (JP) .................. 2020-215177

(51) Int. Cl.
*B65G 1/137* (2006.01)
*B25J 11/00* (2006.01)
*G16H 20/13* (2018.01)

(52) U.S. Cl.
CPC ............ *B65G 1/137* (2013.01); *B25J 11/009* (2013.01); *G16H 20/13* (2018.01)

(58) Field of Classification Search
CPC ...... B25J 11/009; A61G 12/001; B60P 3/007; G16H 20/13; G16H 40/20
See application file for complete search history.

(56) References Cited

U.S. PATENT DOCUMENTS

| | | | |
|---|---|---|---|
| 2018/0333860 A1* | 11/2018 | Jamriska | B25J 11/009 |
| 2019/0205819 A1 | 7/2019 | Igata et al. | |
| 2020/0198150 A1* | 6/2020 | Theobald | B25J 11/008 |
| 2020/0381107 A1* | 12/2020 | Lowry | G06Q 10/08 |

FOREIGN PATENT DOCUMENTS

JP 2019-119537 A 7/2019

* cited by examiner

*Primary Examiner* — Timothy R Waggoner
(74) *Attorney, Agent, or Firm* — Dinsmore & Shohl LLP

(57) ABSTRACT

A management system includes an autonomously movable mobile robot configured to be managed by the management system and transport a transport article. The mobile robot includes a storage locker capable of containing a transport article and being electrically locked or unlocked. The management system is configured to determine whether to unlock the storage locker according to a security level set for unlocking the storage locker. The management system is configured to, when the management system receives a notification of an emergency event, lower the security level.

18 Claims, 7 Drawing Sheets

| TRANSPORT ARTICLE | SECURITY LEVEL (NORMAL TIMES) | SECURITY LEVEL (IN EMERGENCY) |
|---|---|---|
| CONTROLLED MEDICINE (POISONOUS DRUG, POWERFUL DRUG, NARCOTIC DRUG, etc.) | HIGH | MIDDLE |
| ORDINARY MEDICINE | MIDDLE | LOW |
| MEDICAL INSTRUMENT | MIDDLE | LOW |
| SUPPLIES (STATIONERY, etc.) | LOW | — |
| ⋮ | ⋮ | ⋮ |

FIG. 4

| CATEGORY | SECURITY LEVEL (NORMAL TIMES) | SECURITY LEVEL (IN EMERGENCY) |
|---|---|---|
| DOCTOR | LOW | LOW |
| NURSE (NURSE MANAGER CLASS) | LOW | LOW |
| TECHNOLOGIST | MIDDLE | LOW |
| NURSE (OTHER) | MIDDLE | LOW |
| OFFICE WORKER | HIGH | MIDDLE |
| ⋮ | ⋮ | ⋮ |

FIG. 5

| TRANSPORT ARTICLE | SECURITY LEVEL (NORMAL TIMES) | SECURITY LEVEL (IN EMERGENCY) |
|---|---|---|
| CONTROLLED MEDICINE (POISONOUS DRUG, POWERFUL DRUG, NARCOTIC DRUG, etc.) | HIGH | MIDDLE |
| ORDINARY MEDICINE | MIDDLE | LOW |
| MEDICAL INSTRUMENT | MIDDLE | LOW |
| SUPPLIES (STATIONERY, etc.) | LOW | --- |
| ... | ... | ... |

FIG. 6

| TYPE OF NOTIFICATION | DEGREE OF LOWERING SECURITY LEVEL |
|---|---|
| EARTHQUAKE (SEISMIC INTENSITY OF FIVE OR MORE) AND FIRE | 2 |
| EARTHQUAKE (SEISMIC INTENSITY OF FOUR) AND SMALL FIRE | 1 |
| ENTRY OF SUSPICIOUS INDIVIDUALS | 0 |
| ... | ... |

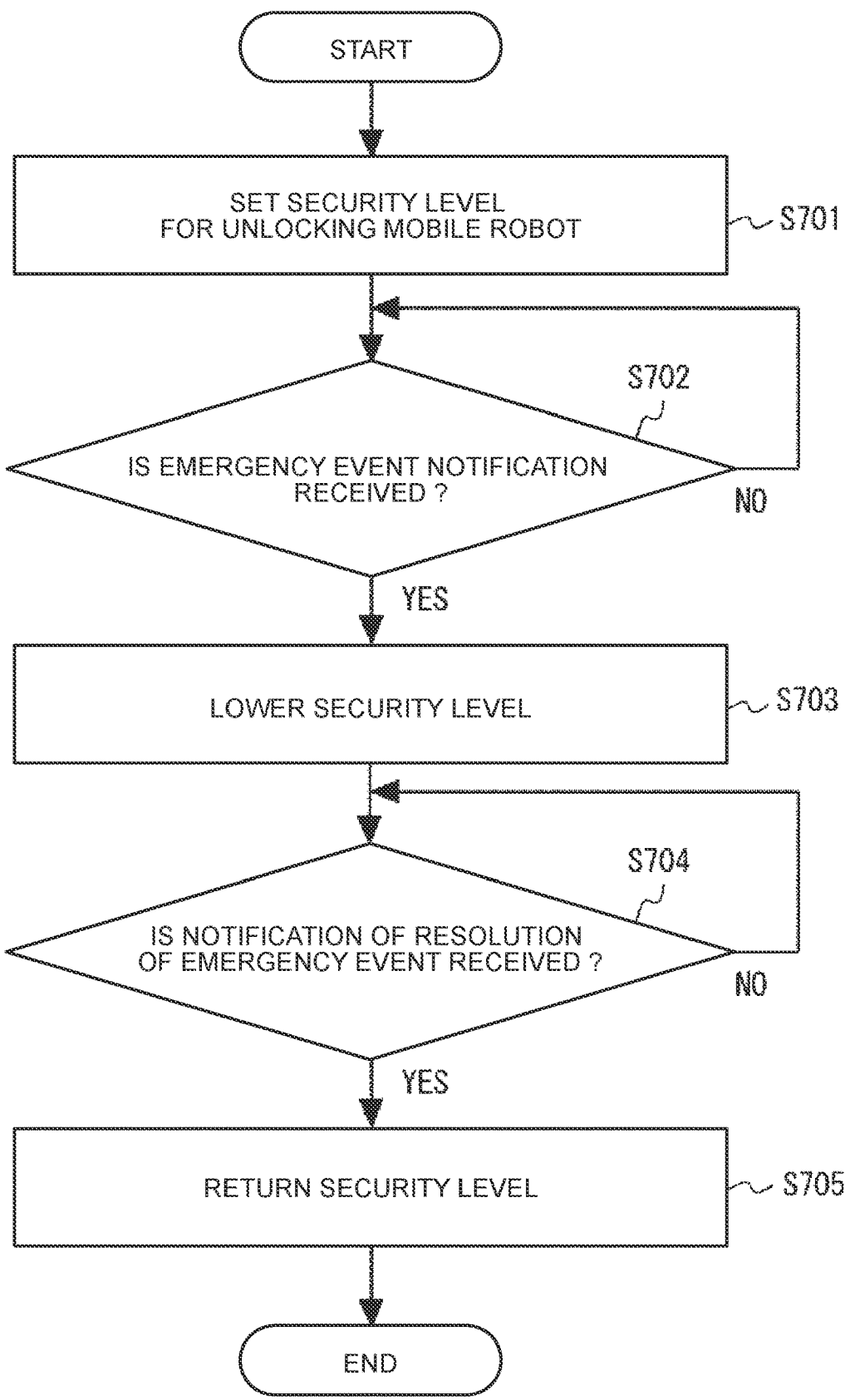

MANAGEMENT SYSTEM, MANAGEMENT METHOD, AND PROGRAM

CROSS-REFERENCE TO RELATED APPLICATION

This application claims priority to Japanese Patent Application No. 2020-215177 filed on Dec. 24, 2020, incorporated herein by reference in its entirety.

BACKGROUND

1. Technical Field

The disclosure relates to a management system, a management method, and a program.

2. Description of Related Art

Japanese Unexamined Patent Application Publication No. 2019-119537 (JP 2019-119537 A) describes a transport method capable of implementing an environment in which a package is handed over easily between individuals while security is ensured. The transport method described in JP 2019-119537 A is a method for causing an autonomous mobile unit including an electrically lockable package storage locker to transport articles. The transport method causes one or more computers to execute a series of steps as follows. In the series of steps, a client requesting the autonomous mobile unit to transport a package is allowed to specify a recipient and pickup location of the package, and the autonomous mobile unit is caused to move to the pickup location specified by the client. In the series of steps, the package storage locker of the autonomous mobile unit having moved to the pickup location is locked when it is determined that the package has been stored in the package storage locker. In the series of steps, the autonomous mobile unit in which the package storage locker is locked is caused to move to a drop-off location specified by the client or the recipient, and the package storage locker of the autonomous mobile unit having moved to the drop-off location is unlocked when the recipient inputs an instruction to unlock the package storage locker.

SUMMARY

However, in the system of JP 2019-119537 A, only a specified recipient can unlock the package storage locker. Thus, in the system described in JP 2019-119537 A, only the recipient can unlock the package storage locker of the autonomous mobile unit even in an emergency. Therefore, when the recipient does other work for emergency response or is absent, the package storage locker cannot be unlocked even in an emergency, and no one can take out a transport article. In other words, as in the case of the system described in JP 2019-119537 A, in a system that does not allow people other than a specified person to unlock a storage locker in a mobile robot that transports a transport article, the specified person often plays a main role in doing other work in an emergency, so no one can handle the transport article in an emergency.

The disclosure provides a management system, a management method, and a program that enable a mobile robot including a storage locker, capable of containing a transport article and being locked or unlocked, to, in setting and managing a target person authorized to unlock the storage locker, allow a transport article to be taken out even when an emergency event occurs and the authorized target person is not able to unlock the storage locker.

A first aspect of the disclosure relates to a management system. The management system includes an autonomously movable mobile robot configured to be managed by the management system. The mobile robot includes a storage locker capable of containing a transport article and being electrically locked or unlocked. The management system is configured to determine whether to unlock the storage locker according to a security level set for unlocking the storage locker. The management system is configured to, when the management system receives a notification of an emergency event, lower the security level. In the management system, with this configuration, when a mobile robot including a storage locker capable of containing a transport article and being locked or unlocked is managed while a target person authorized to unlock the storage locker is set, the transport article is able to be taken out even when an emergency event occurs and the target person authorized to unlock the storage locker is not able to unlock the storage locker.

In the management system, the management system may be configured to, when the management system receives the notification of the emergency event, lower the security level by expanding a range of target persons authorized to unlock the storage locker. Thus, target persons who are able to unlock the storage locker in an emergency can be increased.

In the management system, the management system may be configured to, when the management system receives the notification of the emergency event, lower the security level when a predetermined security level lowering condition is satisfied. Thus, the case where the security level is not lowered even when the notification of the emergency event is received can be provided. The predetermined security level lowering condition may be set for each transport article contained in the storage locker. Thus, whether to lower the security level can be determined for each transport article in an emergency. The management system may be configured to manage the mobile robot such that the mobile robot moves in a hospital, and the predetermined security level lowering condition may be set for each patient who uses a transport article contained in the storage locker. Thus, whether to lower the security level can be determined for each patient in an emergency. The predetermined security level lowering condition may be set for each type of the notification of the emergency event. Thus, whether to lower the security level can be determined for each type of the notification of the emergency event in an emergency.

The management system may be configured to, when the management system receives the notification of the emergency event and lowers the security level and a person, other than a target person authorized to unlock the storage locker before the security level is lowered, unlocks the storage locker, provide a notification to the target person authorized to unlock the storage locker before the security level is lowered. Thus, the target person is able to learn that the storage locker is unlocked.

The management system may be configured to, when the management system receives the notification of the emergency event, lower the security level only for the mobile robot present within a predetermined moving range. Thus, the security level is not lowered for a mobile robot outside the predetermined moving range, so a major issue in terms of security is prevented.

A second aspect of the disclosure relates to a management method that manages an autonomously movable mobile robot. The mobile robot includes a storage locker capable of containing a transport article and being electrically locked or unlocked. The management method includes determining whether to unlock the storage locker according to a security level set for unlocking the storage locker, and, when a notification of an emergency event is received, lowering the security level. In the management method, with this configuration, when a mobile robot including a storage locker capable of containing a transport article and being locked or unlocked is managed while a target person authorized to unlock the storage locker is set, the transport article is able to be taken out even when an emergency event occurs and the target person authorized to unlock the storage locker is not able to unlock the storage locker.

In the management method, when the notification of the emergency event is received, the security level may be lowered by expanding a range of target persons authorized to unlock the storage locker. Thus, target persons who are able to unlock the storage locker in an emergency can be increased.

In the management method, when the notification of the emergency event is received, the security level may be lowered when a predetermined security level lowering condition is satisfied. Thus, the case where the security level is not lowered even when the notification of the emergency event is received can be provided. The predetermined security level lowering condition may be set for each transport article contained in the storage locker. Thus, whether to lower the security level can be determined for each transport article in an emergency. The management method may further include managing the mobile robot such that the mobile robot moves in a hospital. The predetermined security level lowering condition may be set for each patient who uses a transport article contained in the storage locker. Thus, whether to lower the security level can be determined for each patient in an emergency. The predetermined security level lowering condition may be set for each type of the notification of the emergency event. Thus, whether to lower the security level can be determined for each type of the notification of the emergency event in an emergency.

The management method may further include, when the notification of the emergency event is received, the security level is lowered, and a person, other than a target person authorized to unlock the storage locker before the security level is lowered, unlocks the storage locker, providing a notification to the target person authorized to unlock the storage locker before the security level is lowered. Thus, the target person is able to learn that the storage locker is unlocked.

In the management method, when the notification of the emergency event is received, the security level may be lowered only for the mobile robot present within a predetermined moving range. Thus, the security level is not lowered for a mobile robot outside the predetermined moving range, so a major issue in terms of security is prevented.

A third aspect of the disclosure relates to a program that causes a computer to execute a management process of managing an autonomously movable mobile robot. The mobile robot includes a storage locker capable of containing a transport article and being electrically locked or unlocked. The management process includes determining whether to unlock the storage locker according to a security level set for unlocking the storage locker, and, when a notification of an emergency event is received, lowering the security level. In the program, with this process, when a mobile robot including a storage locker capable of containing a transport article and being locked or unlocked is managed while a target person authorized to unlock the storage locker is set, the transport article is able to be taken out even when an emergency event occurs and the target person authorized to unlock the storage locker is not able to unlock the storage locker.

In the management process, when the notification of the emergency event is received, the security level may be lowered by expanding a range of target persons authorized to unlock the storage locker. Thus, target persons who are able to unlock the storage locker in an emergency can be increased.

In the management process, when the notification of the emergency event is received, the security level may be lowered when a predetermined security level lowering condition is satisfied. Thus, the case where the security level is not lowered even when the notification of the emergency event is received can be provided. The predetermined security level lowering condition may be set for each transport article contained in the storage locker. Thus, whether to lower the security level can be determined for each transport article in an emergency. The management process may further include managing the mobile robot such that the mobile robot moves in a hospital. The predetermined security level lowering condition may be set for each patient who uses a transport article contained in the storage locker. Thus, whether to lower the security level can be determined for each patient in an emergency. The predetermined security level lowering condition may be set for each type of the notification of the emergency event. Thus, whether to lower the security level can be determined for each type of the notification of the emergency event in an emergency.

The management process may further include, when the notification of the emergency event is received, the security level is lowered, and a person, other than a target person authorized to unlock the storage locker before the security level is lowered, unlocks the storage locker, providing a notification to the target person authorized to unlock the storage locker before the security level is lowered. Thus, the target person is able to learn that the storage locker is unlocked.

In the management process, when the notification of the emergency event is received, the security level may be lowered only for the mobile robot present within a predetermined moving range. Thus, the security level is not lowered for a mobile robot outside the predetermined moving range, so a major issue in terms of security is prevented.

According to the aspects of the disclosure, it is possible to provide a management system, a management method, and a program that enable a mobile robot including a storage locker, capable of containing a transport article and being locked or unlocked, to, in setting and managing a target person authorize to unlock the storage locker, allow a transport article to be taken out even when an emergency event occurs and the target person authorized to unlock the storage locker is not able to unlock the storage locker.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 4 is a table showing an example of a security level set for each target person;

FIG. 5 is a table showing an example of a security level set for each transport article;

FIG. 6 is a table showing an example of a degree to which a security level is lowered for each type of notification; and FIG. 7 is a flowchart showing an example of a management method according to the embodiment.

DETAILED DESCRIPTION OF EMBODIMENTS

Hereinafter, an embodiment of the disclosure will be described; however, the disclosure is not intended to be limited to the embodiment. All the components of the embodiment are not always indispensable.

Schematic Configuration

Figure 1:
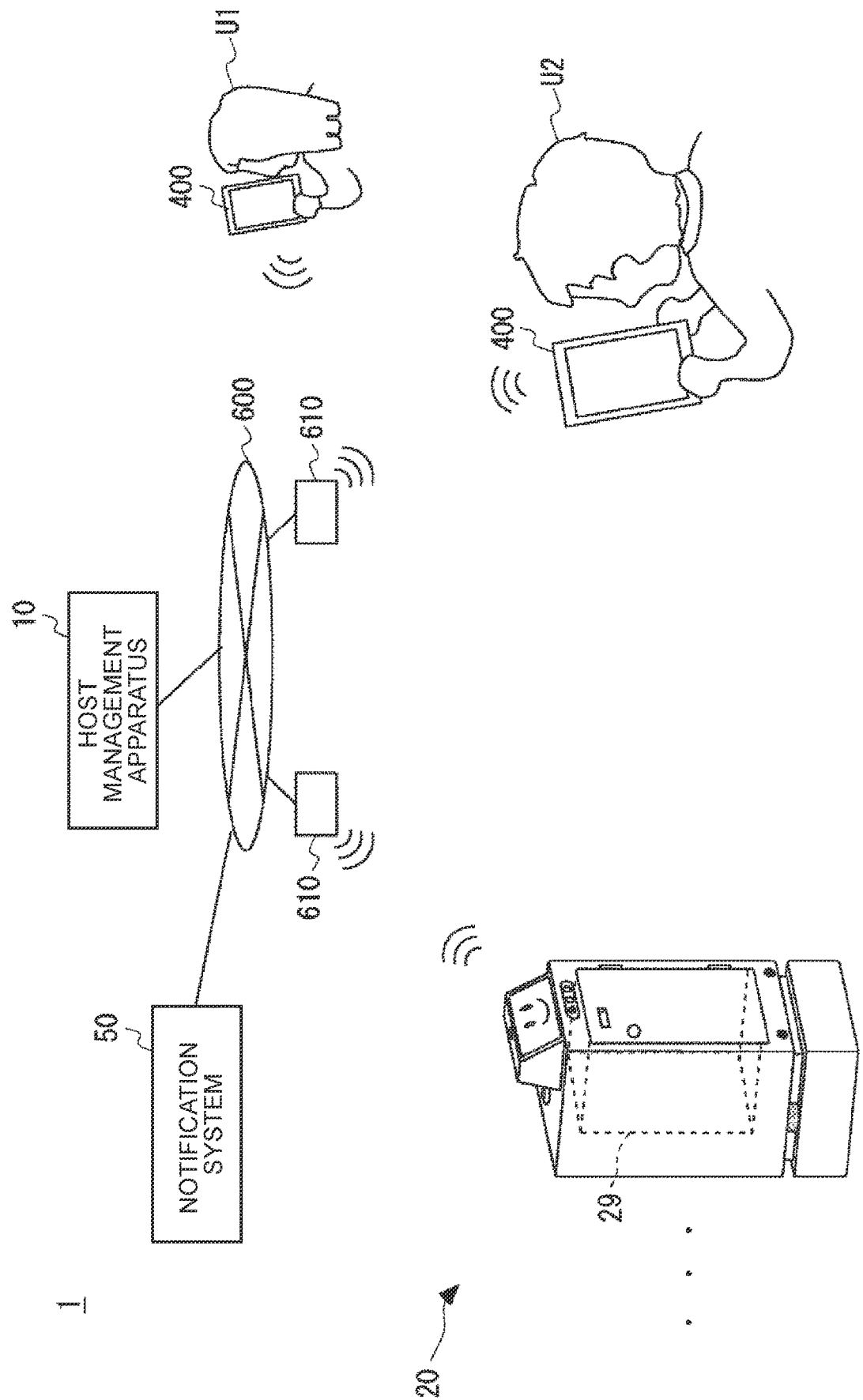
FIG. 1 is a conceptual diagram for illustrating an example of the overall configuration of a management system that manages a mobile robot according to an embodiment.

FIG. 1 is a conceptual diagram for illustrating an example of the overall configuration of a management system 1 that manages a mobile robot 20 according to the present embodiment. The management system 1 according to the present embodiment is a system that manages an autonomously movable mobile robot and is a system that transports a transport article by using the mobile robot. Thus, the management system 1 may also be referred to as transport system. The mobile robot 20 shown in FIG. 1 will be described as an example of the mobile robot. The management system 1 may include one or plurality of mobile robots 20.

The management system 1 includes a notification system 50, a host management apparatus 10, a network 600, communication units 610, and user terminals 400 in addition to the one or plurality of mobile robots 20. The notification system 50 is a system that provides a notification of an emergency event. An emergency event may be an emergency situation, such as an earthquake and a fire; however, the emergency event is not limited thereto.

The mobile robot 20 is a transport robot that transports a transport article as a task, and includes a storage locker 29. The mobile robot 20 autonomously runs to transport a transport article in a medical and welfare facility, such as a hospital, a rehabilitation center, a nursing-care facility, and an elderly living facility. However, the mobile robot 20 may be configured to be able to go outside a facility. The management system 1 according to the present embodiment is also usable in a commercial facility, such as a shopping mall, in a mode not concerned with a process for patients and the like, specialized for hospitals.

The mobile robot 20 used in the present embodiment includes the storage locker 29 capable of containing a transport article and being electrically locked or unlocked. The storage locker 29 can be unlocked by, for example, operation from the user terminal 400, user operation on an operation reception unit 28 (described later) of the mobile robot 20, or other operation. Whether a user is able to take out a transport article, that is, whether to allow a user to unlock the storage locker 29, is determined based on the security level set in advance for a transport article, a target person, or the like.

The management system 1 determines whether to unlock the storage locker 29 according to the security level set for unlocking the storage locker 29. The management system 1 lowers the security level (lowers the security) when the management system 1 receives a notification of an emergency event (emergency event notification) as a major characteristic. This characteristic will be described later.

A user U1, such as a user or manager of a transport article, requests the mobile robot 20 to transport the transport article. The user U1 puts the transport article in the storage locker 29 of the mobile robot 20 at a request location at the time of making a transport request or at a pickup location (transport source) included in information of the transport request. Of course, the transport article can also be loaded by a loading robot or the like.

The mobile robot 20 may be caused to transport various items as transport articles. Examples of the transport articles include medical instruments, drugs, consumables, such as bandages, samples, hospital diets, and supplies, such as stationery. Examples of the medical instruments schematically include an examination tool and a medical tool. The medical instruments include a pressure ulcer prevention device, a sphygmomanometer, a blood infusion pump, an intravenous dripper, such as a syringe pump, a foot pump, a nurse call, a bed exit sensor, a continuous low-pressure inhaler, an electrocardiographic monitor, a drug infusion controller, an enteral nutrition pump, a ventilator, a cuff pressure meter, a touch sensor, an aspirator, a nebulizer, a pulse oximeter, a resuscitator, an aseptic device, an echo device, and the like. Other than these medical instruments, the medical instruments include a surgical tool, such as a catheter, a scalpel knife, and scissors, various intravenous drippers, various vital monitors, and the like.

The mobile robot 20 autonomously moves to a set destination and transports a transport article. In other words, the mobile robot 20 performs a transport task for a package (hereinafter, also simply referred to as task). In the following description, a location where a transport article is loaded is referred to as transport source, and a location where a transport article is delivered is referred to as transport destination.

For example, it is assumed that the mobile robot 20 moves in a general hospital with diagnosis and treatment departments. The mobile robot 20 transports a transport article between diagnosis and treatment departments. For example, the mobile robot 20 delivers a transport article from a nurse station of one diagnosis and treatment department to a nurse station of another diagnosis and treatment department. Alternatively, the mobile robot 20 delivers a medical instrument from a store cabinet to a nurse station of a diagnosis and treatment department. When a transport destination is located on a different floor, the mobile robot 20 may move by using an elevator or the like.

In the present embodiment, as shown in FIG. 1, the notification system 50, the mobile robot 20, and the user terminals 400 are connected to the host management apparatus 10 via the network 600. The notification system 50 can be connected to the host management apparatus 10 and the mobile robot 20 via the network 600. The notification system 50 may be a system partially or entirely implemented in the host management apparatus 10.

The mobile robot 20 and the user terminals 400 are connected to the network 600 via the communication units 610. The network 600 is a wired or wireless local area network (LAN) or wide area network (WAN). The host management apparatus 10 is connected to the network 600 in a wired or wireless manner. Each of the communication units 610 is, for example, a wireless LAN unit installed in each environment. Each of the communication units 610 may be, for example, a general communication device, such as a Wi-Fi router.

Each of the user terminals 400 is, for example, a tablet computer, a smartphone, or the like, or may be a stationary computer. Each of the user terminals 400 just needs to be an information processing apparatus communicable in a wireless or wired manner.

The user U1 or a user U2 is able to make a transport request by using the user terminal 400. For example, the user U1 is able to consult a schedule for a transport request by accessing the notification system 50 (which may intervene the host management apparatus 10) from the user terminal 400 and is able to make a request to the host management apparatus 10 to transport a transport article based on the consulted result. When the host management apparatus 10 receives the transport request, the host management apparatus 10 is able to make a transport request of the mobile robot 20.

In this way, various signals transmitted from the user terminal 400 of the user U1 or the user U2 can be once sent to the host management apparatus 10 via the network 600 and transferred from the host management apparatus 10 to the intended mobile robot 20. Similarly, various signals to be transmitted from the mobile robot 20 are once sent to the host management apparatus 10 via the network 600 and transferred from the host management apparatus 10 to the intended user terminal 400.

The host management apparatus 10 is a server connected to devices and collects data from the devices. The host management apparatus 10 is not limited to a physically single apparatus and may include a plurality of apparatuses that execute distributed processing. The host management apparatus 10 may be implemented so as to be distributed to an edge device such as the mobile robot 20. For example, the management system 1 may be partially or entirely installed in the mobile robot 20.

The user terminal 400 and the mobile robot 20 may transmit and receive signals without intervening the host management apparatus 10. For example, the user terminal 400 and the mobile robot 20 may directly transmit and receive signals by wireless communication. Alternatively, the user terminal 400 and the mobile robot 20 may transmit and receive signals via the communication unit 610.

The user U1 or the user U2 makes a request to transport a transport article by using the user terminal 400. Hereinafter, description will be made on the assumption that the user U1 is a transport client at a transport source and the user U2 is a scheduled recipient at a transport destination (destination). Of course, the user U2 at a transport destination is also able to make a transport request. A user at a location other than the transport source or the transport destination may make a transport request.

When the user U1 makes a transport request, the user U1 enters the details of a transport article, a pickup location of the transport article (hereinafter, also referred to as transport source), a delivery destination of the transport article (hereinafter, also referred to as transport destination), scheduled arrival time at the transport source (pickup time of the transport article), scheduled arrival time at the transport destination (transport time limit), and the like by using the user terminal 400. Hereinafter, these pieces of information are also referred to as transport request information. The transport source may be set to a storage location of the transport article. The transport source may be a location where the user U1 is present. The transport destination is a location where the user U2 or a patient who is scheduled to use the transport article. The user U1 is able to enter transport request information by operating a touch panel of the user terminal 400.

The user terminal 400 is able to transmit the transport request information entered by the user U1 to the host management apparatus 10. The host management apparatus 10 is a management system that manages a plurality of the mobile robots 20 and transmits an operation command for performing a transport task to each mobile robot 20. At this time, the host management apparatus 10 chooses the mobile robot 20 to perform a transport task for each transport request. Then, the host management apparatus 10 transmits a control signal containing an operation command to the mobile robot 20. The mobile robot 20 moves from the transport source to reach the transport destination in accordance with the operation command.

For example, the host management apparatus 10 assigns a transport task to the mobile robot 20 at a transport source or around the transport source. Alternatively, the host management apparatus 10 assigns a transport task to the mobile robot 20 heading to a transport source or around the transport source. The mobile robot 20 to which the task is assigned goes to the transport source to pick up a transport article. The transport source is, for example, a storage location or a location where the user U1 who has made a request for the task is present.

When the mobile robot 20 reaches the transport source, the user U1 or another staff loads a transport article in the mobile robot 20. The mobile robot 20 loaded with the transport article autonomously moves with the transport destination set for a destination. The host management apparatus 10 transmits a signal to the user terminal 400 of the user U2 at the transport destination. Thus, the user U2 is able to learn that the transport article is being transported and the scheduled arrival time. When the mobile robot 20 reaches the set transport destination, the user U2 is able to receive the transport article contained in the mobile robot 20. In this way, the mobile robot 20 performs the transport task.

In the above-described overall configuration, the elements of the management system 1 may be distributed among the mobile robots 20, the user terminals 400, the notification system 50, and the host management apparatus 10 to construct a system as a whole. Alternatively, substantial elements for achieving transport of a transport article may be gathered and constructed in a single apparatus. The host management apparatus 10 controls one or plurality of mobile robots 20.

Control Block Diagram

Figure 2:
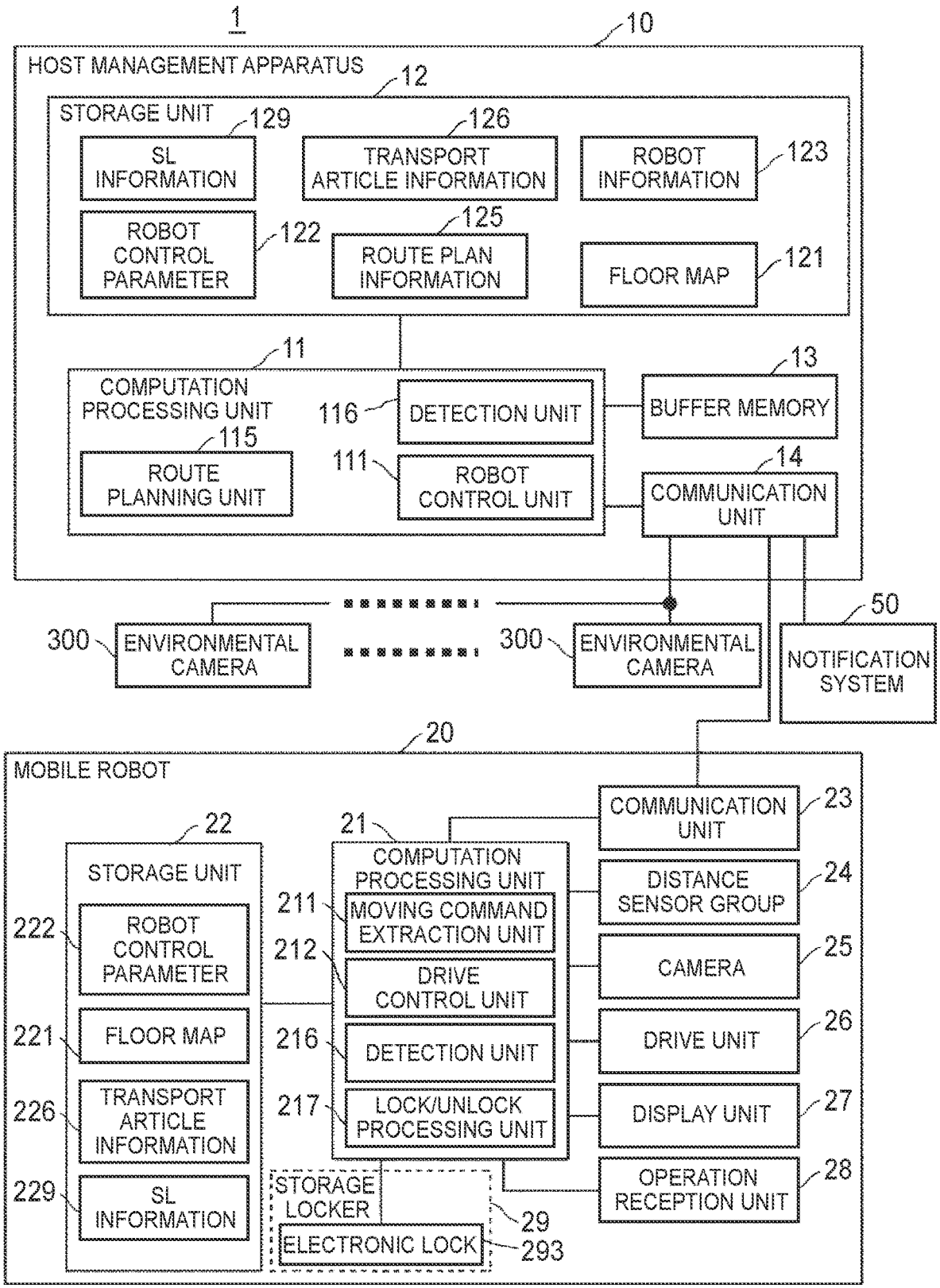
FIG. 2 is a control block diagram showing an example of the management system according to the embodiment.

FIG. 2 is a control block diagram showing an example of a control system of the management system 1. As shown in FIG. 2, the management system 1 may include the host management apparatus 10, the mobile robots 20, the notification system 50, and environmental cameras 300.

The management system 1 efficiently controls the mobile robots 20 while causing the mobile robots 20 to autonomously move in a predetermined facility. For this reason, the plurality of environmental cameras 300 is installed in the facility. For example, the environmental cameras 300 are installed at passages, halls, elevators, entrances, and the like in the facility.

The environmental cameras 300 acquire images in a range in which each mobile robot 20 moves. In the management system 1, the host management apparatus 10 collects images acquired by the environmental cameras 300 and information based on the images. Alternatively, images and the like acquired by the environmental cameras 300 may be directly transmitted to the mobile robots 20. The environmental cameras 300 may be surveillance cameras and the like provided at passages and entrances in the facility. The environmental cameras 300 may be used to find a distribution of crowdedness in the facility.

In the management system 1, the host management apparatus 10 makes a route plan based on transport request information and generates route plan information. The host management apparatus 10 provides instructions to the mobile robots 20 on destinations based on the generated route plan information. The mobile robots 20 autonomously move toward the destinations specified by the host management apparatus 10. Each of the mobile robots 20 autonomously moves toward the destination by using a sensor provided in itself, a floor map, location information, and the like.

For example, each of the mobile robots 20 runs so as not to contact with a device, an object, a wall, or a person around the mobile robot 20 (hereinafter, collectively referred to as surrounding object). Specifically, each of the mobile robots 20 detects a distance to the surrounding object and runs at a certain distance (distance threshold) or longer from the surrounding object. When the distance to the surrounding object becomes shorter than or equal to the distance threshold, the mobile robot 20 decelerates or stops. With this configuration, each of the mobile robots 20 is capable of running without contacting with the surrounding object. Since each of the mobile robots 20 is capable of avoiding the contact, the mobile robot 20 is able to safely and efficiently transport a transport article.

The host management apparatus 10 may include a computation processing unit 11, a storage unit 12, a buffer memory 13, and a communication unit 14. The computation processing unit 11 performs computation for controlling and managing the mobile robots 20. The computation processing unit 11 can be implemented as, for example, a unit capable of running programs, such as a central processing unit (CPU) of a computer. Various functions can be implemented by programs. FIG. 2 shows only characteristic units, that is, a robot control unit 111, a route planning unit 115, and a detection unit 116 in the computation processing unit 11, and the computation processing unit 11 further includes other processing blocks.

The robot control unit 111 performs computation for remotely controlling each of the mobile robots 20 and generates a control signal. The robot control unit 111 generates a control signal based on route plan information 125 (described later) and the like. The robot control unit 111 generates a control signal additionally based on various pieces of information obtained from the environmental cameras 300 and the mobile robots 20. A control signal may contain update information of a floor map 121, robot information 123, a robot control parameter 122 (described later), and the like. In other words, when various pieces of information are updated, the robot control unit 111 generates a control signal according to the update information.

The route planning unit 115 plans the route of each mobile robot 20. When a transport task is entered, the route planning unit 115 plans a route for transporting a transport article to a transport destination (destination) based on transport request information. Specifically, the route planning unit 115 chooses the mobile robot 20 to perform a new transport task by consulting the route plan information 125, robot information 123, and the like already stored in the storage unit 12. A point of departure is a current location of the mobile robot 20, a transport destination of a last transport task, a pickup location of a transport article, or the like. A destination is a transport destination of a transport article and may also be a waiting location, a charging location, or the like.

Here, the route planning unit 115 sets passage points of each mobile robot 20 from the point of departure to the destination. The route planning unit 115 sets the order of passage of the passage points for each mobile robot 20. The passage point is set to, for example, a branch point, an intersection, a lobby in front of an elevator, or around these locations. In a narrow-width passage, the mobile robots 20 can be difficult to pass by each other. In such a case, a location just before the narrow-width passage may be set for a passage point. Candidates of passage points may be registered in the floor map 121 in advance.

The route planning unit 115 chooses the mobile robot 20 to perform each transport task from among the plurality of mobile robots 20 so that the tasks are efficiently performed as an overall system. The route planning unit 115 preferentially assigns a transport task to the mobile robot 20 in waiting or the mobile robot 20 located near a transport source.

The route planning unit 115 sets passage points including a point of departure and a destination for the mobile robot 20 to which a transport task is assigned. When, for example, there are two or more moving routes from a transport source to a transport destination, passage points are set such that the mobile robot 20 is able to move in a shorter time. Therefore, the host management apparatus 10 updates information indicating the crowdedness of a passage based on images from the cameras, and the like. Specifically, the degree of crowdedness is high in a place where another mobile robot 20 is passing or a place where there are many people. Therefore, the route planning unit 115 sets passage points such that places having a high degree of crowdedness are avoided.

The mobile robot 20 can be able to move to a destination along any of a clockwise moving path and a counterclockwise moving path. In such a case, the route planning unit 115 sets passage points such that the mobile robot 20 passes along an uncrowded one of the moving paths. When the route planning unit 115 sets one or plurality of passage points along a route to the destination, the mobile robot 20 is able to move along the uncrowded moving path. When, for example, a passage is branching at a branch point or an intersection, the route planning unit 115 sets a passage point to the branch point, the intersection, a corner, or a location around that point. Thus, transport efficiency is improved.

The route planning unit 115 may set passage points in consideration of the crowdedness of elevators, a moving distance, and the like. The host management apparatus 10 may estimate the number of mobile robots 20 and the number of people at schedule time at which the mobile robot 20 passes through a certain point. Then, the route planning unit 115 may set passage points according to the estimated crowdedness. The route planning unit 115 may dynamically change passage points according to a change in crowdedness. The route planning unit 115 sequentially sets passage points for the mobile robot 20 to which a transport task is assigned. Passage points may include a transport source and a transport destination. The mobile robot 20 autonomously moves so as to sequentially pass through the passage points set by the route planning unit 115.

The detection unit 116 detects a notification of an emergency event (emergency event notification) transmitted from the notification system 50 and received by the communication unit 14. When the detection unit 116 detects such a notification, the robot control unit 111 transmits a control signal to the mobile robot 20 via the communication unit 14. The control signal contains a security level lowering command to cause the mobile robot 20 to lower the security level for unlocking the storage locker 29. In advance of transmitting a control signal containing such a security level lowering command, the robot control unit 111 is capable of incorporating information indicating to lower the security level into security level (SL) information 129 (described later) at the stage where the detection unit 116 detects the notification and is capable of generating the signal by consulting the SL information 129. Alternatively, the SL information 129 may include both information before the security level is lowered and information after the security level is lowered, and the robot control unit 111 may be configured to, at the stage where the detection unit 116 detects the notification, change so as to consult information after the security level is lowered.

The storage unit 12 is a storage unit that stores information needed to manage and control robots. In the example of FIG. 2, the floor map 121, the robot information 123, the robot control parameter 122, the route plan information 125, transport article information 126, and the security level (SL) information 129 are shown; however, information stored in the storage unit 12 may include other information. The computation processing unit 11 performs computation using information stored in the storage unit 12 in executing various processes. Various pieces of information stored in the storage unit 12 can be updated with the latest information.

The floor map 121 is map information of a facility in which the mobile robots 20 are moved. The floor map 121 may be the one created in advance, may be the one generated from information obtained from the mobile robots 20, or may be the one obtained by adding map correction information, generated from information obtained from the mobile robots 20, to a base map created in advance. The floor map 121 may include map information outside the facility. In this case, information indicating whether the location is inside the facility or outside the facility is configured to be read out.

The robot information 123 includes the ID, model number, specifications, and the like of each of the mobile robots 20 managed by the host management apparatus 10. The robot information 123 may include location information indicating the current location of each mobile robot 20. The robot information 123 may include information as to whether each mobile robot 20 is performing a task or waiting. The robot information 123 may include information indicating whether each mobile robot 20 is in operation, in failure, or the like. The robot information 123 may include information about a transportable article and a non-transportable article.

The robot control parameter 122 includes control parameters such as a threshold distance from a surrounding object to each of the mobile robots 20 managed by the host management apparatus 10. The threshold distance is a margin distance for avoiding contact with surrounding objects including people. The robot control parameter 122 may include information on operation strength, such as a speed upper limit of the moving speed of each mobile robot 20.

The robot control parameter 122 may be updated according to a situation. The robot control parameter 122 may include information indicating the status of vacancy and status of use of the storage space of the storage locker 29 capable of actually containing a transport article in a storage cabinet 291 (described later). The robot control parameter 122 may include information about a transportable article and a non-transportable article. Of course, the robot control parameter 122 may include information indicating whether another transport article, other than the transport article, can be transported or not. The robot control parameter 122 associates the various pieces of information with each of the mobile robots 20.

The route plan information 125 includes route plan information planned by the route planning unit 115. The route plan information 125, for example, includes information indicating a transport task. The route plan information 125 may include information on the ID of the mobile robot 20 to which a task is assigned, a point of departure, transport article details, a transport destination, a transport source, scheduled arrival time at the transport destination, scheduled arrival time at the transport source, an arrival limit, and the like. In the route plan information 125, the various pieces of information may be associated with each transport task. The route plan information 125 may include at least part of transport request information input from the user U1.

The route plan information 125 may include information about passage points for each of the mobile robots 20 and the transport tasks. For example, the route plan information 125 includes information indicating the order of passage of passage points for each of the mobile robots 20. The route plan information 125 may include the coordinates of each passage point in the floor map 121 and information as to whether the passage point is passed.

The transport article information 126 is information about a transport article for which a transport request is made. The transport article information 126 includes, for example, information on transport article details (type), a transport source, a transport destination, and the like. The transport article information 126 may include the ID of the mobile robot 20 in charge of transport. The transport article information 126 may include information indicating a status such as transporting, before transporting (before loading), and transported. The transport article information 126 associates these pieces of information with each transport article.

The route planning unit 115 makes a route plan by consulting various pieces of information stored in the storage unit 12. The route planning unit 115, for example, chooses the mobile robot 20 to perform a task based on the floor map 121, the robot information 123, the robot control parameter 122, and the route plan information 125. The route planning unit 115 sets passage points up to the transport destination and the order of passage by consulting the floor map 121 and the like. Candidates of passage points are registered in the floor map 121 in advance. The route planning unit 115 sets passage points according to crowdedness and the like. When, for example, tasks are successively processed, the route planning unit 115 may set a transport source and a transport destination as passage points.

Two or more mobile robots 20 may be allocated to a single transport task. When, for example, a transport article is larger than the transportable capacity of the mobile robot 20, one transport article is split into two and loaded on two mobile robots 20. Alternatively, when, for example, a transport article is heavier than the transportable weight of the mobile robot 20, one transport article is split into two and loaded on two mobile robots 20. With this configuration, two or more mobile robots 20 are able to respectively perform shares of a single transport task. Of course, when mobile robots 20 having different sizes are controlled, a route may be planned such that the mobile robot 20 capable of transporting a transport article picks up the transport article.

One mobile robot 20 may perform two or more transport tasks in parallel. For example, one mobile robot 20 may be loaded with two or more transport articles at the same time and sequentially transport the transport articles to different transport destinations. Alternatively, one mobile robot 20 may be loaded with another transport article while transporting one transport article. Transport destinations of transport articles respectively loaded at different locations may be the same or may be different. With this configuration, a task is efficiently performed.

In such a case, storage information indicating the status of use or the status of vacancy may be updated for the storage space of each mobile robot 20. In other words, the host management apparatus 10 may manage storage information indicating the status of vacancy and control the mobile robots 20. When, for example, loading or pickup of a transport article completes, storage information is updated. When a transport task is entered, the host management apparatus 10 causes the mobile robot 20 having space for loading a transport article to go to pick up by consulting the storage information. With this configuration, one mobile robot 20 is able to perform multiple transport tasks at the same time or two or more mobile robots 20 are able to perform shares of a transport task. For example, a sensor may be installed in the storage space of each mobile robot 20, and the status of vacancy may be detected. The capacity and weight of a transport article may be registered in advance for each transport article.

The security level (SL) information 129 is information indicating the security level set for unlocking the storage locker 29. The security level is a level in taking out a transport article, that is, handling a transport article and can be set for a transport article, a target person, or the like. In the present embodiment, the description will be made on the assumption that, in the case of an object (a transport article, a target person, or the like) of which the security level is high, target persons authorized to take out a transport article reduce; whereas, in the case of an object of which the security level is low, target persons authorized to take out a transport article increase. An example of the SL information 129 will be described later.

The buffer memory 13 is a memory that accumulates intermediate information to be generated in a process executed by the computation processing unit 11. The communication unit 14 is a communication interface for communicating with a plurality of environmental cameras 300 and at least one mobile robot 20, provided in a facility in which the management system 1 is operated. The communication unit 14 is capable of performing both wired communication and wireless communication. For example, the communication unit 14 transmits a control signal needed to control each mobile robot 20 to the mobile robot 20. The communication unit 14 receives information collected by the mobile robots 20 and the environmental cameras 300. The communication unit 14 is capable of receiving an emergency event notification from the notification system 50.

Each mobile robot 20 may include a computation processing unit 21, a storage unit 22, a communication unit 23, a proximity sensor (for example, a distance sensor group 24), a camera 25, a drive unit 26, a display unit 27, and an operation reception unit 28. FIG. 2 shows only typical processing blocks included in each mobile robot 20. Each mobile robot 20 also includes many other processing blocks (not shown).

The communication unit 23 is a communication interface for communicating with the communication unit 14 of the host management apparatus 10. The communication unit 23 communicates with the communication unit 14 by using, for example, a radio signal. The distance sensor group 24 is, for example, a proximity sensor and outputs approaching object distance information indicating a distance to an object or a person present around the mobile robot 20. The camera 25, for example, captures an image for acquiring a situation around the mobile robot 20. The camera 25 is capable of capturing, for example, a positional marker provided on a ceiling or the like of the facility. The positional marker may be used to make the mobile robot 20 to acquire the location of its own.

The communication unit 23 may be configured to receive an emergency event notification from the notification system 50. Thus, the detection unit 216 (described later) is able to directly detect an occurrence of an emergency event and lower the security level even without receiving a security level lowering command based on the emergency event notification from the host management apparatus 10.

The drive unit 26 drives drive wheels provided for the mobile robot 20. The drive unit 26 may include an encoder or the like that detects the rotation speed of each of the drive wheels or drive motors for the drive wheels. Its own location (current location) may be estimated according to an output of the encoder. The mobile robot 20 detects its current location and transmits the current location to the host management apparatus 10.

The display unit 27 and the operation reception unit 28 are implemented by a touch panel display. The display unit 27 displays a user interface screen serving as the operation reception unit 28. The display unit 27 may be caused to display information indicating the destination of the mobile robot 20 and the status of the mobile robot 20. The operation reception unit 28 receives operations from a user. The operation reception unit 28 includes various switches provided for the mobile robot 20 in addition to the user interface screen displayed on the display unit 27.

Operations to be received by the operation reception unit 28 may include an operation to unlock the storage locker 29. With this configuration, an electronic lock 293 (described later) is controlled from the operation reception unit 28. However, in the present embodiment, the security level for unlocking the storage locker 29 is set as described above, and not all the users are authorized to unlock the storage locker 29.

The computation processing unit 21 performs computation used to control the mobile robot 20. The computation processing unit 21 can be implemented as, for example, a unit capable of running programs, such as a central processing unit (CPU) of a computer. Various functions can be implemented by programs. The computation processing unit 21 includes the detection unit 216, a lock/unlock processing unit 217, a moving command extraction unit 211, and a drive control unit 212. FIG. 2 shows only typical processing blocks of the computation processing unit 21. The computation processing unit 21 further includes processing blocks (not shown). The computation processing unit 21 may search for a route between passage points.

The moving command extraction unit 211 extracts a moving command from a control signal given from the host management apparatus 10. For example, a moving command includes information about the next passage point. For example, a control signal may include coordinates of passage points and information about the order of passage of the passage points. The moving command extraction unit 211 extracts these pieces of information as a moving command.

A moving command may include information indicating that movement to the next passage point is enabled. When a passage width is narrow, the mobile robots 20 may not be able to pass by each other. A passage may be temporarily impassable. In such a case, a control signal contains a command to stop the mobile robot 20 at a passage point before a location to be stopped. Then, after another mobile robot 20 passes by or the passage becomes passable, the host management apparatus 10 outputs, to the mobile robot 20, a control signal informing that the mobile robot 20 is allowed to move. Thus, the temporarily stopped mobile robot 20 resumes moving.

The drive control unit 212 controls the drive unit 26 such that the mobile robot 20 is moved based on the moving command given from the moving command extraction unit 211. For example, the drive unit 26 includes drive wheels that rotate according to a control command value from the drive control unit 212. The moving command extraction unit 211 extracts a moving command such that the mobile robot 20 moves toward the passage point received from the host management apparatus 10. Then, the drive unit 26 drives the drive wheels for rotation. The mobile robot 20 autonomously moves toward the next passage point. In this way, the mobile robot 20 sequentially passes through the passage points and reaches the transport destination. The mobile robot 20 may estimate its own location and transmit, to the host management apparatus 10, a signal indicating passage of a passage point. Thus, the host management apparatus 10 is able to manage the current location and transport status of each mobile robot 20.

The detection unit 216 detects (extracts) a security level lowering command from a control signal given from the host management apparatus 10. The security level lowering command is a command to lower the security level. When a security level lowering command is detected, the computation processing unit 21 lowers the security level by updating the security level (SL) information 229 in the storage unit 22.

The electronic lock 293 is configured to be capable of locking or unlocking the storage locker 29. When the lock/unlock processing unit 217 receives an unlock operation from the operation reception unit 28 or an unlock operation from the user terminal 400, the lock/unlock processing unit 217 controls the electronic lock 293 in accordance with the security level set by the SL information 229 by consulting the SL information 229 and, when being allowed to unlock the storage locker 29, cause the electronic lock 293 to unlock the storage locker 29. When the lock/unlock processing unit 217 receives a lock operation from the operation reception unit 28 or a lock operation from the user terminal 400, the lock/unlock processing unit 217 controls the electronic lock 293 and causes the electronic lock 293 to lock the storage locker 29. The electronic lock 293 just needs to have a mechanism capable of electrically locking or unlocking, and the configuration of the electronic lock 293 does not matter. The electronic lock 293 may employ, for example, a mechanism that locks or unlocks through near field communication with an electronic key (for example, an IC card) or the like of a user.

The storage unit 22 stores a floor map 221, a robot control parameter 222, transport article information 226, and SL information 229. FIG. 2 shows only part of information stored in the storage unit 22. The information stored in the storage unit 22 further includes information other than the floor map 221, the robot control parameter 222, or the transport article information 226, shown in FIG. 2. The floor map 221 is map information of the facility in which the mobile robots 20 are moved. The floor map 221 is, for example, data obtained by downloading part or all of the floor map 121 of the host management apparatus 10. The floor map 221 may be created in advance. The floor map 221 may be not map information of the whole facility and may be map information partially including a region in which the mobile robot 20 is scheduled to move.

The robot control parameter 222 is a parameter for operating the mobile robot 20. The robot control parameter 222 includes, for example, a distance threshold to a surrounding object. The robot control parameter 222 further includes a speed upper limit of the mobile robot 20.

The transport article information 226 includes information about a transport article, similar to the transport article information 126. The transport article information 226 may include information on transport article details (type, that is, model), a transport source, a transport destination, and the like. The transport article information 226 may include information indicating a status such as transporting, before transporting (before loading), and transported. The transport article information 226 associates these pieces of information with each transport article. The transport article information 226 just needs to include information about a transport article to be transported by the mobile robot 20. Therefore, the transport article information 226 is part of the transport article information 126. In other words, the transport article information 226 does not need to include information about a transport article to be transported by another mobile robot 20.

The drive control unit 212 consults the robot control parameter 222 and stops or decelerates the operation in response to the fact that the distance indicated by the distance information obtained from the distance sensor group 24 becomes shorter than the distance threshold. The drive control unit 212 controls the drive unit 26 such that the mobile robot 20 runs at a speed lower than or equal to the speed upper limit. The drive control unit 212 limits the rotation speed of each of the drive wheels such that the mobile robot 20 does not move at a speed higher than or equal to the speed upper limit.

The security level (SL) information 229, as well as the SL information 129, is information indicating the security level set for unlocking the storage locker 29 and does not need to include information indicating the security level set for unlocking the storage locker 29 in another mobile robot 20. The security level of the SL information 229 just needs to be brought into coincidence with the security level of the SL information 129 by timely consulting the SL information 129.

The notification system 50 may include a system with which, for example, public entities, such as municipalities and government ministries, provide a notification of disaster information. In this case, the communication unit 14 of the host management apparatus 10 or both the communication unit 14 and the communication unit 23 of the mobile robot 20 are capable of acquiring disaster information provided by the system via the network 600 or the like. The notification system 50 may be a transmitter of a television broadcast signal. In this case, when the host management apparatus 10 or both the host management apparatus 10 and the mobile robot 20 are configured to receive a television broadcast signal and, when emergency report information is included the television broadcast signal, extract the information, the host management apparatus 10 or both the host management apparatus 10 and the mobile robot 20 are able to acquire the emergency report information.

The notification system 50 may include one or plurality of fire alarms respectively installed at one or plurality of locations in the facility. In this case, the communication unit 14 of the host management apparatus 10 or both the communication unit 14 and the communication unit 23 of the mobile robot 20 may be configured to receive a notification signal from the one or plurality of fire alarms. The one or plurality of fire alarms may be managed by a facility management system that manages the facility. The host management apparatus 10 may include the facility management system or may be constructed as an integrated management system that manages the facility management system in an integrated manner.

As illustrated here, when the facility is a hospital, the notification system 50 may include a facility management system that makes an emergency call (an in-house alarm indicating that the hospital is placed in an emergency framework). In this case, the communication unit 14 of the host management apparatus 10 or both the communication unit 14 and the communication unit 23 of the mobile robot 20 may be configured to receive an emergency call from the facility management system.

As in the case of these examples, the management system 1 may be constructed as an integrated management system that manages a plurality of mobile robots 20 and a facility management system that manages a facility (building). With this configuration, pieces of information about the facility and the plurality of mobile robots 20 are aggregated, signals of information and commands are transmitted to the plurality of mobile robots 20 based on the information provided from the facility management system, and an emergency situation is determined based on a notification from the facility management system managed by the management system 1.

Configuration of Mobile Robot 20

Figure 3:
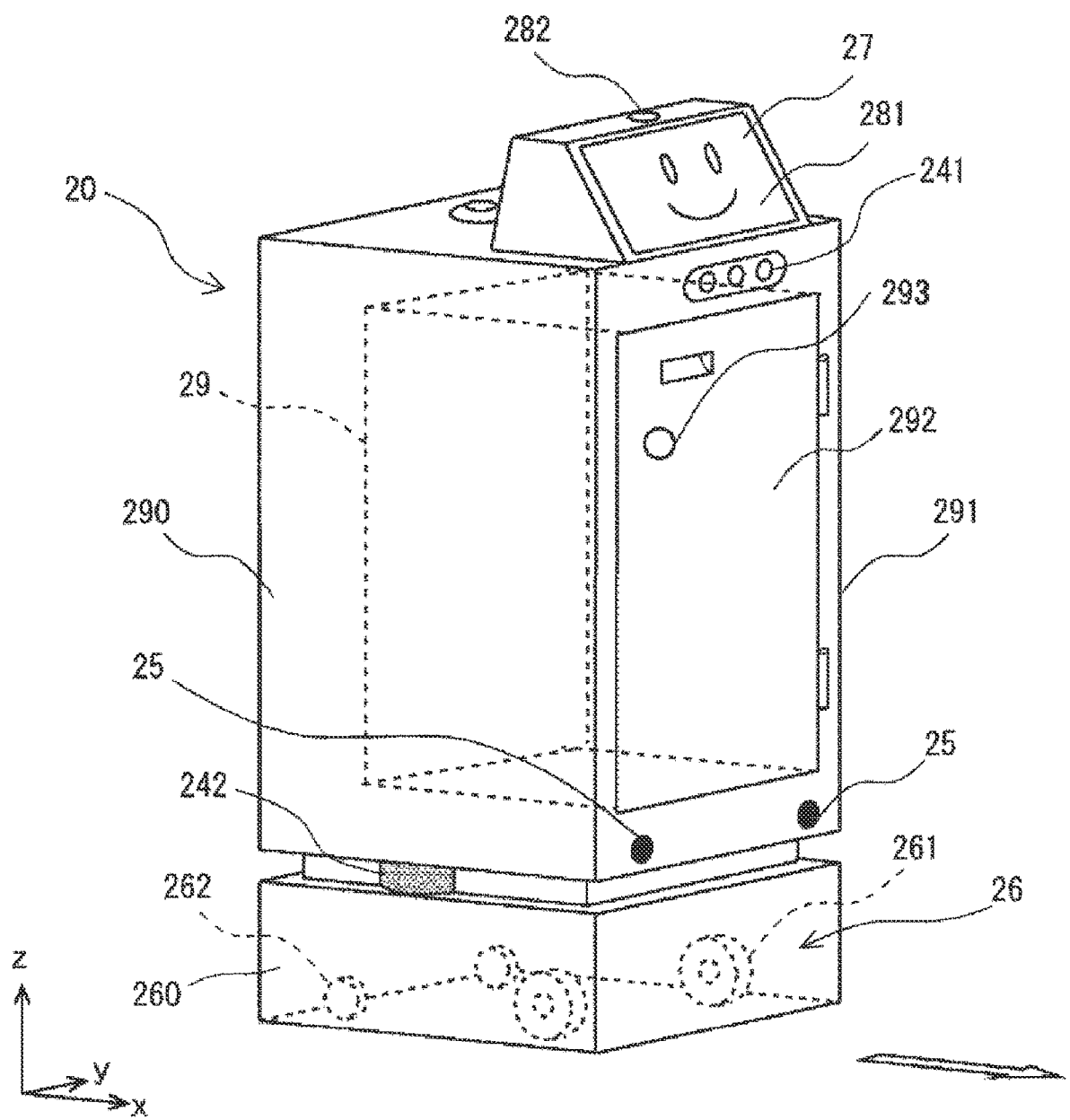
FIG. 3 is a schematic view showing an example of the mobile robot.

Here, the appearance of the mobile robot 20 will be described. FIG. 3 shows a schematic view of the mobile robot 20. The mobile robot 20 shown in FIG. 3 is one form of the mobile robot 20. The mobile robot 20 may be another form. In FIG. 3, the x direction corresponds to the forward and reverse directions of the mobile robot 20, the y direction corresponds to the right and left direction of the mobile robot 20, and the z direction corresponds to the height direction of the mobile robot 20.

The mobile robot 20 includes a body portion 290 and a carriage portion 260. The body portion 290 is mounted on the carriage portion 260. Each of the body portion 290 and the carriage portion 260 has a rectangular-parallelepiped housing. Component elements of each of the body portion 290 and the carriage portion 260 are installed in the housing. For example, the drive unit 26 is accommodated in the carriage portion 260.

The body portion 290 includes the storage cabinet 291 and a door 292. The storage cabinet 291 has the storage locker 29 that is a storage space. The door 292 hermetically seals the storage cabinet 291. A plurality of shelves is provided in the storage locker 29, and the status of vacancy is managed for each shelf. When, for example, various sensors, such as a weight sensor, are installed at each shelf, the status of vacancy can be updated. The mobile robot 20 transports a transport article contained in the storage locker 29 by autonomously moving to a destination provided through an instruction from the host management apparatus 10. A control box (not shown) or the like may be installed in the housing of the body portion 290.

The electronic lock 293 may be provided at the door 292 and is capable of locking or unlocking with an electronic key or the like. When the mobile robot 20 reaches a transport destination, the user U2 unlocks the door 292 with the electronic key. The door 292 is allowed to be unlocked when the user U2 is a recipient or when the user U2 is authorized to unlock the door 292.

As shown in FIG. 3, front-rear distance sensors 241 and right-left distance sensors 242 are provided on the exterior of the mobile robot 20 as the distance sensor group 24. The mobile robot 20 measures a distance to a surrounding object in the front and rear direction of the mobile robot 20 with the front-rear distance sensors 241. The mobile robot 20 measures a distance to a surrounding object in the right and left direction of the mobile robot 20 with the right-left distance sensors 242.

For example, the front-rear distance sensor 241 is disposed on each of the front side and rear side of the housing of the body portion 290. The right-left distance sensor 242 is disposed on each of the right side and left side of the housing of the body portion 290. The front-rear distance sensors 241 and the right-left distance sensors 242 each are, for example, an ultrasonic distance sensor or a laser range finder. Each of the front-rear distance sensors 241 and the right-left distance sensors 242 detects a distance to a surrounding object. When a distance to a surrounding object, detected by any one of the front-rear distance sensors 241 and the right-left distance sensors 242, becomes shorter than or equal to the distance threshold, the mobile robot 20 decelerates or stops.

The drive unit 26 includes drive wheels 261 and casters 262. The drive wheels 261 are wheels for moving the mobile robot 20 forward, rearward, rightward, or leftward. Driving force is not supplied to the casters 262. The casters 262 are driven wheels that roll following the drive wheels 261. The drive unit 26 includes drive motors (not shown) and drives the drive wheels 261.

For example, the drive unit 26 supports the two drive wheels 261 and the two casters 262 in the housing. Each of the drive wheels 261 and the casters 262 contacts with a running surface. The two drive wheels 261 are disposed such that the rotation axes coincide with each other. Each of the drive wheels 261 is driven for rotation by the motor (not shown) independently. The drive wheels 261 rotate in accordance with a control command value from the drive control unit 212 of FIG. 2. Each of the casters 262 is a driven wheel and is provided so as to pivotally support the wheel such that the pivot axis extending in the vertical direction from the drive unit 26 is located away from the rotation axis of the wheel. The casters 262 follow so as to be aligned in the moving direction of the drive unit 26.

The mobile robot 20, for example, moves straight ahead when the two drive wheels 261 are rotated in the same direction at the same rotation speed and turns around a vertical axis passing through substantially the center of the two drive wheels 261 when the drive wheels 261 are rotated in opposite directions at the same rotation speed. When the two drive wheels 261 are rotated in the same direction at different rotation speeds, the mobile robot 20 is able to move while turning right or left. When, for example, the rotation speed of the left drive wheel 261 is higher than the rotation speed of the right drive wheel 261, the mobile robot 20 is able to turn right. On the other hand, when the rotation speed of the right drive wheel 261 is higher than the rotation speed of the left drive wheel 261, the mobile robot 20 is able to turn left. In other words, when the rotation directions and rotation speeds of the two drive wheels 261 are controlled, the mobile robot 20 is able to, for example, translate, swivel, turn right, or turn left in a selected direction.

In the mobile robot 20, the display unit 27 and an operation interface 281 are provided on the top side of the body portion 290. The operation interface 281 is displayed on the display unit 27. When a user touches to operate the operation interface 281 displayed on the display unit 27, the operation reception unit 28 is able to receive an instruction entered by the user. An emergency stop button 282 is provided on the top side of the display unit 27. The emergency stop button 282 and the operation interface 281 function as the operation reception unit 28.

The display unit 27 is, for example, a liquid crystal panel. The display unit 27 displays the face of a character by illustration or represents information about the mobile robot 20 by text or icon. When the face of a character is displayed on the display unit 27, the display unit 27 is able to give the impression that the face of the character is a pseudo-face to a surrounding observer. The display unit 27 or the like, installed in the mobile robot 20, may be used as the user terminal 400.

The cameras 25 are installed on the front side of the body portion 290. Here, the two cameras 25 function as a stereo camera. In other words, the two cameras 25 having the same angle of view are disposed apart from each other in the horizontal direction. The cameras 25 respectively output captured images as image data. A distance to a subject and the size of the subject can be calculated based on the image data of the two cameras 25. The computation processing unit 21 is capable of detecting a person, an obstacle, and the like ahead in the moving direction by analyzing the images of the cameras 25. When there is a person, an obstacle, and the like ahead in the moving direction, the mobile robot 20 moves along a route while avoiding them. The image data of the cameras 25 is transmitted to the host management apparatus 10.

The mobile robot 20 recognizes a surrounding object or identifies the location of its own by analyzing image data output from the cameras 25 and detection signals output from the front-rear distance sensors 241 and the right-left distance sensors 242. The cameras 25 respectively capture images ahead in the moving direction of the mobile robot 20. As shown in the drawing, the front side of the mobile robot 20 is a side on which the cameras 25 are installed. In other words, during normal moving, as indicated by the arrow, the front side of the mobile robot 20 corresponds to the moving direction.

Main Characteristics of Present Embodiment

Next, the main characteristics of the present embodiment in the management system 1 configured as described above will be described. The main characteristics of the present embodiment are not only determining whether to unlock the storage locker 29 according to the security level set for unlocking the storage locker 29 but also lowering the security level when an emergency event notification is received. These controls can be performed when, for example, the host management apparatus 10 serves as a subject to control the mobile robot 20 and such an example is described here and can also be performed by, for example, the mobile robot 20 as a subject.

An example of set security levels and lowering of the security levels will be described with reference to FIG. 4 to FIG. 6. FIG. 4 is a table showing an example of the security level set for each target person. FIG. 5 is a table showing an example of the security level set for each transport article. FIG. 6 is a table showing an example of a degree to which the security level is lowered for each type of notification. For the sake of simple description, an example in which the security level is set to any one of three levels, that is, high, medium, and low will be described; however, the number of levels does not matter. The SL information 129 or the SL information 229 can be illustrated by, for example, one or some of the tables shown in FIG. 4 to FIG. 6.

As illustrated in FIG. 4, target persons for which the security level is set may be a doctor, a nurse (nurse manager class), a nurse (other), an office worker, and the like, and the security levels "low", "low", "medium", "medium", and "high", can be respectively set during normal times (when the security level is not lowered). For example, a doctor, for which the security level is set to "low", is allowed to access the electronic lock 293 and unlock the electronic lock 293 even in any case, and an office worker, for which the security level is set to "high", is almost not allowed to access the electronic lock 293 and unlock the electronic lock 293.

When the host management apparatus 10 receives an emergency event notification in this state, the host management apparatus 10 transmits a control signal containing a security level lowering command to the mobile robot 20. The mobile robot 20 is able to lower the security levels (make it easy to unlock) by setting the security levels of doctor, nurse (nurse manager class), nurse (other), and office worker to "low", "low", "low", "low", and "middle", based on the security level lowering command. Examples of the target persons may include a clinical technologist, a clinical radiologist, an occupational therapist, a physical therapist, a clinical engineer, an assistant nurse, and an engineer of a maker of an instrument.

In this way, when the management system 1 receives an emergency event notification, the management system 1 may lower the security levels by expanding a range of target persons authorized to unlock the storage locker 29 (authorized to take out a transport article). Thus, target persons who are able to unlock the storage locker 29 in an emergency can be increased.

When the management system 1 receives an emergency event notification, the management system 1 may lower the security levels when a predetermined security level lowering condition (a condition for lowering the security level) is satisfied. Thus, the case where the security level is not lowered even when an emergency event notification is received may be provided.

For example, the predetermined security level lowering condition may be set for each of transport articles contained in the storage locker 29. For example, the security level of one transport article is lowered for only target persons for which the security level is set to "high", and the security level of another transport article is lowered for persons for which the security level is set to any of "high", "middle", and "low". In this way, the security level is not uniformly changed, and a condition for lowering the security level is allowed to be set for each transport article. Thus, it is possible to minutely set whether to lower the security level for each transport article in an emergency. Here, the security level may be lowered when the security level of at least one of transport articles contained at the same time is allowed to be lowered. The security level may be lowered when the security level of all or a predetermined ratio (for example, 50%) or higher of transport articles contained at the same time is allowed to be lowered.

An example of setting and lowering the security level of each transport article will be described. As illustrated in FIG. 5, the security level may be set for each transport article. In this example, during normal times (when the security level is not lowered), the security levels, that is, "high", "middle", "middle", and "low", can be respectively set for transport articles of a controlled medicine (a poisonous drug, a powerful drug, a narcotic drug, and the like), another ordinary medicine, a medical instrument, and supplies (stationery and the like).

When the host management apparatus 10 receives an emergency event notification in this state, the host management apparatus 10 transmits a control signal containing a security level lowering command to the mobile robot 20. The mobile robot 20 is able to lower the security levels (make it easy to unlock) by setting the security levels of a controlled medicine, an ordinary medicine, a medical instrument, and supplies to "medium", "low", "low", and "none", based on the security level lowering command. When the security levels are not sufficiently lowered as in the case of this example, the lowest security level is set.

The predetermined security level lowering condition may be set for each type of emergency event notification. A type of notification means a type of emergency event. Examples of the type of notification include types of earthquake, fire, and emergency code and may be further minutely handled as types of large earthquake, medium-scale earthquake, large fire, small fire, and various color emergency codes. For example, for a notification of one type, security levels for only target persons for which the security level is set to "high" are lowered, and, for a notification of the other type, security levels for target persons for which the security level is set to any of "high", "medium", and "low" are lowered. Thus, whether to lower the security level can be minutely determined according to the type of the notification in an emergency.

The degree to which the security level is lowered may be set for each type of emergency event notification. As illustrated in FIG. 6, the degree to which the security level is lowered can be set for each type of notification. In this example, the security levels can be lowered by two steps, one step, and zero steps respectively for occurrences of emergency events, that is, earthquake with a seismic intensity of five or more or fire, earthquake with a seismic intensity of four or small fire, and entry of suspicious individuals. Lowering the security level by two steps means that the security level is changed from "high" to "low".

The predetermined security level lowering condition may be set for each patient who uses a transport article contained in the storage locker 29. For example, the security level of a transport article for one patient is lowered for only a target person for which the security level is set to "high", and the security level of a transport article for another patient is lowered for a person for which the security level is set to any of "high", "middle", and "low". In this way, when the facility is a hospital, the security level is not uniformly changed, and a condition for lowering the security level is configured to be set for each patient who uses a transport article. Thus, whether to lower the security level can be minutely determined for each patient in an emergency.

When the management system 1 receives an emergency event notification, the management system 1 may set, for each transport article contained in the storage locker 29, whether to lower the security level. In this way, the security level is not uniformly changed, and whether to lower the security level is set for each transport article. Thus, for example, a transport article for which the security level is not lowered in any case, such as a poisonous drug, can be set. In this case, when the security level of at least one of transport articles contained is not lowered, it is desirable not to lower the security level.

Whether to lower the security level in the case where an emergency event notification is received may be set for each patient who uses a transport article contained in the storage locker 29. In this way, when the facility is a hospital, the security level is not uniformly changed, and whether to lower the security level can be set for each patient who uses a transport article. Thus, it is possible not to lower the security level in any case for a transport article to be used for a specific patient. In this case as well, when the security level of at least one of transport articles contained is not lowered, it is desirable not to lower the security level.

When the management system 1 receives an emergency event notification and lowers the security level and a person, other than a target person authorized to unlock the storage locker 29 before the security level is lowered, unlocks the storage locker 29, the management system 1 may provide a notification to the target person authorized to unlock the storage locker 29 before the security level is lowered. When a person, other than a person who belongs to the security level before the security level is lowered, unlocks the storage locker 29 in this way, a notification is provided to the person who belongs to the security level before the security level is lowered, and the target person is able to learn that the storage locker 29 is unlocked. Therefore, the target person is able to deal with the situation when there is some trouble or when the transport article is needed.

When the management system 1 receives an emergency event notification, the management system 1 may lower the security level of only the mobile robots 20 present in a predetermined moving range. Thus, the security level is not lowered for the mobile robots 20 outside the predetermined moving range (for example, outside the facility), so a major issue in terms of security is prevented. Determination as to whether the location is inside the facility or outside the facility can be performed by consulting the floor map 121 or the floor map 221.

According to the present embodiment, when the mobile robot 20 including the storage locker 29 capable of containing a transport article and being locked or unlocked is managed while a target person authorized to unlock the storage locker 29 is set, the transport article is able to be taken out even when an emergency event occurs and the target person authorized to unlock the storage locker 29 is not able to unlock the storage locker 29. Particularly, in a system in which only a specific person is able to unlock a transport robot in an emergency, the specific person often plays a main role in doing other work in an emergency, so there are concerns that no one can handle the transport article in an emergency. However, in the present embodiment, the security level is lowered, so such concerns are reduced. When the degree or the like to which the security level is lowered is enabled to be set, a person who does not matter in handling a transport article is able to handle the transport article in consideration of safety, so the specific person is not bothered.

Management Method

FIG. 7 is a flowchart showing an example of a management method according to the present embodiment. Initially, the host management apparatus 10 or the mobile robot 20 sets the security level for unlocking the mobile robot 20 (S701). Subsequently, the host management apparatus 10 or the mobile robot 20 determines whether an emergency event notification is received (S702), and waits until an emergency event notification is received. When the notification is received (YES in S702), the host management apparatus 10 causes the managed mobile robot 20 to lower the security level (S703). Alternatively, in S703, the mobile robot 20 may receive a notification and lower the security level.

Subsequently, the host management apparatus 10 or the mobile robot 20 determines whether a notification of resolution cancellation of an emergency event is received (S704), and waits until the notification is received. When the notification is received (YES in S704), the host management apparatus 10 causes the managed mobile robot 20 to cancel the lowering of the security level (S705), and then ends the process. Alternatively, in S705, the mobile robot 20 may receive such a notification and cancel the lowering of the security level. Cancellation of the lowering of the security level may be configured to be performed by a manager having predetermined access authority from the host management apparatus 10, or the mobile robot 20, or the user terminal 400.

Part or all of processes in the host management apparatus 10, the mobile robot 20, the notification system 50, and the like can be implemented as a computer program. The above program can be stored in various types of non-transitory computer readable media and can be supplied to a computer. The non-transitory computer readable media include various types of tangible storage media. Examples of the non-transitory computer readable media include a magnetic recording medium (such as a flexible disk, a magnetic tape, and a hard disk drive), a magnetooptical recording medium (such as a magneto-optical disk), a read only memory (CD-ROM), a CD-R, CD-R/W, a semiconductor memory (such as a mask ROM, a programmable ROM (PROM), an erasable PROM (EPROM), a flash ROM, and a random access memory (RAM)). The program may be supplied to a computer via various types of transitory computer readable media. Examples of the transitory computer readable media include an electrical signal, an optical signal, and an electromagnetic wave. A transitory computer readable medium is able to supply the program to a computer via a wired communication path, such as an electric wire and an optical fiber, or a wireless communication path.

The disclosure is not limited to the above-described embodiment and may be modified as needed without departing from the scope of the disclosure. For example, the management system according to the present embodiment is not limited to the case where the mobile robot 20 configured as described above is used. Instead of or in addition to this configuration, a variously-configured mobile robots respectively having variously-configured storage lockers capable of being locked or unlocked may be used. In the above-described embodiment, the system in which the mobile robot autonomously moves mainly in a hospital is described; however, the transport system may transport a transport article in a hotel, a restaurant, an office building, an event site, or a complex facility. The description is made on the assumption that a transport article is transported in one facility; however, as long as a mobile robot is capable of moving between a plurality of facilities, the transport system is similarly applicable to transportation between the plurality of facilities. Examples of the target person include a doctor, a nurse, and a technologist; however, these names vary among countries, and categories and medicines that persons in each category are allowed to handle also vary.

What is claimed is:

1. A management system comprising:
   an autonomously movable mobile robot configured to be managed by the management system, wherein:
   the mobile robot includes a storage locker capable of containing a transport article and being electrically locked or unlocked;
   the management system is configured to determine whether to unlock the storage locker according to a security level set for unlocking the storage locker; and
   the management system is configured to, when the management system receives a notification of an emergency event, lower the security level when a predetermined security level lowering condition is satisfied, the predetermined security level lowering condition is set for each transport article contained in the storage locker.

2. The management system according to claim 1, wherein the management system is configured to, when the management system receives the notification of the emergency event, lower the security level by expanding a range of target persons authorized to unlock the storage locker.

3. The management system according to claim 1, wherein:
   the management system is configured to manage the mobile robot such that the mobile robot moves in a hospital; and
   the predetermined security level lowering condition is set for each patient who uses a transport article contained in the storage locker.

4. The management system according to claim 1, wherein the predetermined security level lowering condition is set for each type of the notification of the emergency event.

5. The management system according to claim 1, wherein the management system is configured to, when the management system receives the notification of the emergency event and lowers the security level and a person, other than a target person authorized to unlock the storage locker before the security level is lowered, unlocks the storage locker, provide a notification to the target person authorized to unlock the storage locker before the security level is lowered.

6. The management system according to claim 1, wherein the management system is configured to, when the management system receives the notification of the emergency event, lower the security level only for the mobile robot present within a predetermined moving range.

7. A management method of managing an autonomously movable mobile robot, the mobile robot including a storage locker capable of containing a transport article and being electrically locked or unlocked, the management method comprising:
   determining whether to unlock the storage locker according to a security level set for unlocking the storage locker; and
   when a notification of an emergency event is received, lowering the security level when a predetermined security level lowering condition is satisfied, the predetermined security level lowering condition is set for each transport article contained in the storage locker.

8. The management method according to claim 7, wherein, when the notification of the emergency event is received, the security level is lowered by expanding a range of target persons authorized to unlock the storage locker.

9. The management method according to claim 7, further comprising managing the mobile robot such that the mobile robot moves in a hospital, wherein the predetermined security level lowering condition is set for each patient who uses a transport article contained in the storage locker.

10. The management method according to claim 7, wherein the predetermined security level lowering condition is set for each type of the notification of the emergency event.

11. The management method according to claim 7, further comprising, when the notification of the emergency event is received, the security level is lowered, and a person, other than a target person authorized to unlock the storage locker before the security level is lowered, unlocks the storage locker, providing a notification to the target person authorized to unlock the storage locker before the security level is lowered.

12. The management method according to claim 7, wherein, when the notification of the emergency event is received, the security level is lowered only for the mobile robot present within a predetermined moving range.

13. A non-transitory storage medium storing instructions that are executed by a computer and that cause the computer to execute a management process of managing an autonomously movable mobile robot, the mobile robot including a storage locker capable of containing a transport article and being electrically locked or unlocked, the management process comprising:

determining whether to unlock the storage locker according to a security level set for unlocking the storage locker;

when a notification of an emergency event is received, lowering the security level when a predetermined security level lowering condition is satisfied, the predetermined security level lowering condition is set for each patient who uses a transport article contained in the storage locker; and managing the mobile robot such that the mobile robot moves in a hospital.

14. The non-transitory storage medium according to claim 13, wherein, in the management process, when the notification of the emergency event is received, the security level is lowered by expanding a range of target persons authorized to unlock the storage locker.

15. The non-transitory storage medium according to claim 13, wherein, in the management process, the predetermined security level lowering condition is set for each transport article contained in the storage locker.

16. The non-transitory storage medium according to claim 13, wherein the predetermined security level lowering condition is set for each type of the notification of the emergency event.

17. The non-transitory storage medium according to claim 13, wherein the management process further comprises, when the notification of the emergency event is received, the security level is lowered, and a person, other than a target person authorized to unlock the storage locker before the security level is lowered, unlocks the storage locker, providing a notification to the target person authorized to unlock the storage locker before the security level is lowered.

18. The non-transitory storage medium according to claim 13, wherein, in the management process, when the notification of the emergency event is received, the security level is lowered only for the mobile robot present within a predetermined moving range.

\* \* \* \* \*